(12) United States Patent
Cerutti et al.

(10) Patent No.: US 6,852,507 B1
(45) Date of Patent: Feb. 8, 2005

(54) RECOMBINANT BACULOVIRUS AND USE THEREOF IN THE PRODUCTION OF MONOCLONAL ANTIBODIES

(75) Inventors: Martine Cerutti, Saint-Christol-les-Ales (FR); Hassan Chaabihi, Ales (FR); Gerard Devauchelle, Saint-Chistol-les-Ales (FR); Laurent Gauthier, Ales (FR); Michel Kaczorek, Montferrier (FR); Marie-Paule LeFranc, Clapiers (FR); Marie-Alix Poul, Castries (FR)

(73) Assignees: L'Institut National de la Recherche Agronomique; Le Centre National de la Recherche Scientifique (FR)

( * ) Notice: Subject to any disclaimer, the term of this patent is extended or adjusted under 35 U.S.C. 154(b) by 0 days.

(21) Appl. No.: 08/975,982

(22) Filed: Nov. 21, 1997

Related U.S. Application Data

(63) Continuation of application No. 08/807,864, filed on Feb. 26, 1997, now abandoned, which is a continuation of application No. 08/687,354, filed on Jul. 31, 1996, now abandoned, which is a continuation of application No. PCT/FR95/00110, filed on Jan. 31, 1995.

(30) Foreign Application Priority Data

Jan. 31, 1994 (FR) .............................. 94 01015

(51) Int. Cl.$^7$ .......................... C12P 21/00; C12P 21/08; C12N 15/866; C12N 15/63
(52) U.S. Cl. ................ 435/69.1; 435/235.1; 435/320.1; 435/455; 435/456; 435/69.6; 435/69.7; 435/69.8; 435/325; 435/348; 530/350; 530/387.1; 530/387.3; 536/23.1; 536/23.4; 536/23.5; 536/24.1

(58) Field of Search .......................... 435/235.1, 320.1, 435/455, 456, 69.1, 69.6, 69.8, 69.7, 325, 348; 530/350, 387.1, 387.3; 536/23.1, 23.4, 23.5, 24.1

(56) References Cited

U.S. PATENT DOCUMENTS 5,229,272 A * 7/1993 Paul et al. ................. 435/68.1
6,312,690 B1 * 11/2001 Edelman et al. ......... 424/142.1

OTHER PUBLICATIONS

Carayannopoulos et al., PNAS, Aug. 1994, vol. 91, pp. 8348–8352.*

Charles A. Hasemann et al, High–level production of a functional immunoglobulin heterodimer in a baculovirus expression system, vol. 87, pp. 3942–3946, May 1990.*

* cited by examiner

*Primary Examiner*—David Guzo
(74) *Attorney, Agent, or Firm*—Piper Rudnick LLP

(57) ABSTRACT

Recombinant baculovirus used as an expression vector in the production of immunoglobulins with an insect cell. The invention is characterized by a first expression cassette comprising a first sequence coding for at least one portion of an immunoglobulin heavy chain, wherein the sequence is transcriptionally controlled by a first baculovirus promoter, and a second expression cassette comprising a second sequence coding for at least one portion of an immunoglobulin light chain, said second sequence being transcriptionally controlled by a second baculovirus promoter. The first and second promoters are two different promoters or derivatives of different promoters, the first and second promoters residing at different loci.

14 Claims, 5 Drawing Sheets

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 76 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

ATCAAATAAA TAAGTATTTT AAAGAATTCG TACGTATTTT GTATATTAAT TAAAATACTA   60

```
TACTGTAAAT AGATCG                                              76

(2) INFORMATION FOR SEQ ID NO: 2:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GATCCGATCT ATTTACAGTA TAGTATTTTA ATTAATATAC AAAATACGTA CGAATTCTTT    60

AAAATACTTA TTTATTTGAT                                              80

(2) INFORMATION FOR SEQ ID NO: 3:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

ATGGGATGGA GCTGTATCAT CCTCTTCTTG GTAGCAACAG CTACAGGTGT CCACTCC       57

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

AGCTCGAGAT CAAACGG                                              17

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GAAGATCTAA CACTCTCCGC GGTTGAAG                                  28

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

CCTGTCAGAT CTATGAACAT TCTGTAGGGG                                30
```

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CCGCCCTCCC TCGAGCTTCA A                                        21

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CASTCTGAGC TCACKCAG                                            18

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

TTGAAGCTCC TCGAGGGAGG GCGGGAA                              27

(2) INFORMATION FOR SEQ ID NO: 10:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 10:

ATGGCTGTCC TGGTGCTGTT CCTCTGCCTG GTTGCATTTC CCAGCTGTGT CCACTCC        57

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

CAAGGTACCA CGGTCACCGT CTCC                                     24

(2) INFORMATION FOR SEQ ID NO: 12:

(i) SEQUENCE CHARACTERISTICS:

```
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GAAGATCTCA TTTACCCGGA GACAGGGAG                                          29

(2) INFORMATION FOR SEQ ID NO: 13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GAAGATCTCA TTTACCGGGA TTTACAGA                                           28

(2) INFORMATION FOR SEQ ID NO: 14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GAAGATCTCA TTTACCGGTG GACTTGTCGT C                                       31

(2) INFORMATION FOR SEQ ID NO: 15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GAAGATCTCA GTAGCAGGTG CCGTCCACCT C                                       31

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CCGTTTGATC TCGAGCTTGG TCCC                                               24

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

```
            (ii) MOLECULE TYPE: DNA (genomic)

(xi) SEQUENCE DESCRIPTION: SEQ ID NO: 17:

GACATTCAGC TCACCCAGTC TCCA                                                      24

(2) INFORMATION FOR SEQ ID NO: 18:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 18:

TGAGGAGACG GTGACCGTGG TACCTTGGC                                                 29

(2) INFORMATION FOR SEQ ID NO: 19:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 19:

AGGTSMARCT GCAGSAGTCW GG                                                        22
```

RECOMBINANT BACULOVIRUS AND USE THEREOF IN THE PRODUCTION OF MONOCLONAL ANTIBODIES

CROSS-REFERENCE TO RELATED APPLICATIONS

This application is a continuation of U.S. patent application Ser. No. 08/807,864, filed Feb. 26, 1997, now abandoned, which in turn is a continuation of U.S. patent application Ser. No. 08/687,354, filed Jul. 31, 1996, now abandoned, which is a continuation of PCT/FR95/00110, filed Jan. 31, 1995, which claims priority from French patent application serial number 94/01015, filed Jan. 31, 1994.

BACKGROUND OF THE INVENTION

1. Field of the Invention

The present invention relates to a modified baculovirus and to its use for the production of immunoglobulins.

2. Description of Related Art

Antibodies or immunoglobulins are produced by B lymphocytes. Each B lymphocyte secretes a single type of antibody. Each immunoglobulin molecule is constituted of the combination of two heavy chains (H) and two light chains (L) connected by disulfide bridges. Each chain is constituted of a variable region (VH and VL) which contains the antigen attachment site and a constant region (CH and CL). There are many types of heavy chains ($\gamma 1$, $\gamma 2$, $\gamma 3$, $\gamma 4$, $\alpha$, $\epsilon$, $\mu$) which define the various classes of immunoglobulins (IgG1, IgG2, IgG3, IgG4, IgA, IgE, IgM . . . ) and two types of light chains: kappa chain ($\kappa$) and lambda chain ($\lambda$). For example, the IgG1 class antibodies are constituted of two heavy chains of the $\gamma 1$ type and two kappa $\kappa$ or lambda $\lambda$ light chains. The variable regions are responsible for the specificity of the antibody for its antigen.

For each chain of a given antibody, the variable region has many domains, certain of which are preserved to varying degrees. The rearrangement of these variable regions is the result of a recombination at the level of the genomic DNA of the B lymphocytes.

Monoclonal antibodies are conventionally produced from cultures of hybridoma lines, with each line derived from a single B lymphocyte and secreting a single type of immunoglobulin.

Monoclonal antibodies (mAbs) are commonly used at present for in vitro diagnostics, and their use in therapy and for in vivo diagnostics shows promising developments. These developments, however, are held back by the fact that the only monoclonal antibodies that are relatively easily available in adequate quantities from hybridoma cultures are monoclonal antibodies from rodents. However, these rodent immunoglobulins (and nonhuman immunoglobulins in general) induce an undesirable immune response in humans which considerably limits their therapeutic value.

Extensive research has been carried out with the goal of obtaining immunoglobulins that do not have this drawback; specifically, it has been proposed to employ genetic engineering techniques to fabricate recombinant antibodies in which the largest possible part of the molecule is derived from a gene of human origin.

The resultant antibodies, in which only the variable domains are of non-human origin, are referred to as chimeric antibodies. There also exist antibodies referred to as human in which the sequences of the variable regions not directly involved in the recognition of the antigen have been replaced by sequences of human origin. In both cases, the greatest part of the immunoglobulin molecule is derived from a gene of human origin.

Nevertheless, the production of antibodies using genetic engineering requires the selection of a suitable host in order to ensure that the post-translational modifications required to reproduce the properties of the native antibody are made. For this purpose, it has been proposed, among other approaches, to employ the baculovirus/insect cell system.

Baculoviruses are widely used as vectors for the expression of heterologous genes, placed under the control of viral promoters, in the cells of infected insects. The promoter of the genes encoding polyhedrin or p10, proteins produced in large amounts during the late phase of the viral replication cycle, is thus frequently used for this purpose.

HASEMAN and CAPRA [Proc. Natl. Acad. Sci. USA, 87, 3942–3946 (1990)], PUTLITZ et al. [Bio/Technology, 8, 651–654 (1990)], and REIS et al. [Bio/Technology, 10, 910–912 (1992)] thus constructed baculoviruses in which were inserted at a single locus two copies of the polyhedrin promoter, with one of these copies controlling the expression of a gene coding for the heavy chain of a mouse immunoglobulin and the other copy controlling the expression of a gene coding for the light chain of the same immunoglobulin. The insect cells infected by these baculoviruses secreted immunoglobulins that had essentially the same properties as the antibodies of lymphocytic origin employed as the model. However, the structure of the baculoviruses modified in this manner is not maintained beyond several cycles of viral replication.

BRIEF SUMMARY OF THE INVENTION

The goal of the present invention is to produce both the heavy chain (H) and the light chain (L) of a given antibody in an insect cell, by employing an expression vector derived from a baculovirus that does not exhibit the drawbacks of the expression vectors of the same type used in the prior art for the production of immunoglobulins.

To attain this goal, the inventors constructed double-recombinant baculoviruses in which the coding sequences of the two H and L chains are situated at different loci of the genome of the baculovirus, and each chain is placed under the control of a different strong promoter (in contrast to the baculoviruses of the prior art cited above in which the two chains are placed in the same locus of the genome of a baculovirus and under control of two copies of the same promoter).

DETAILED DESCRIPTION OF THE INVENTION

Figure 1:
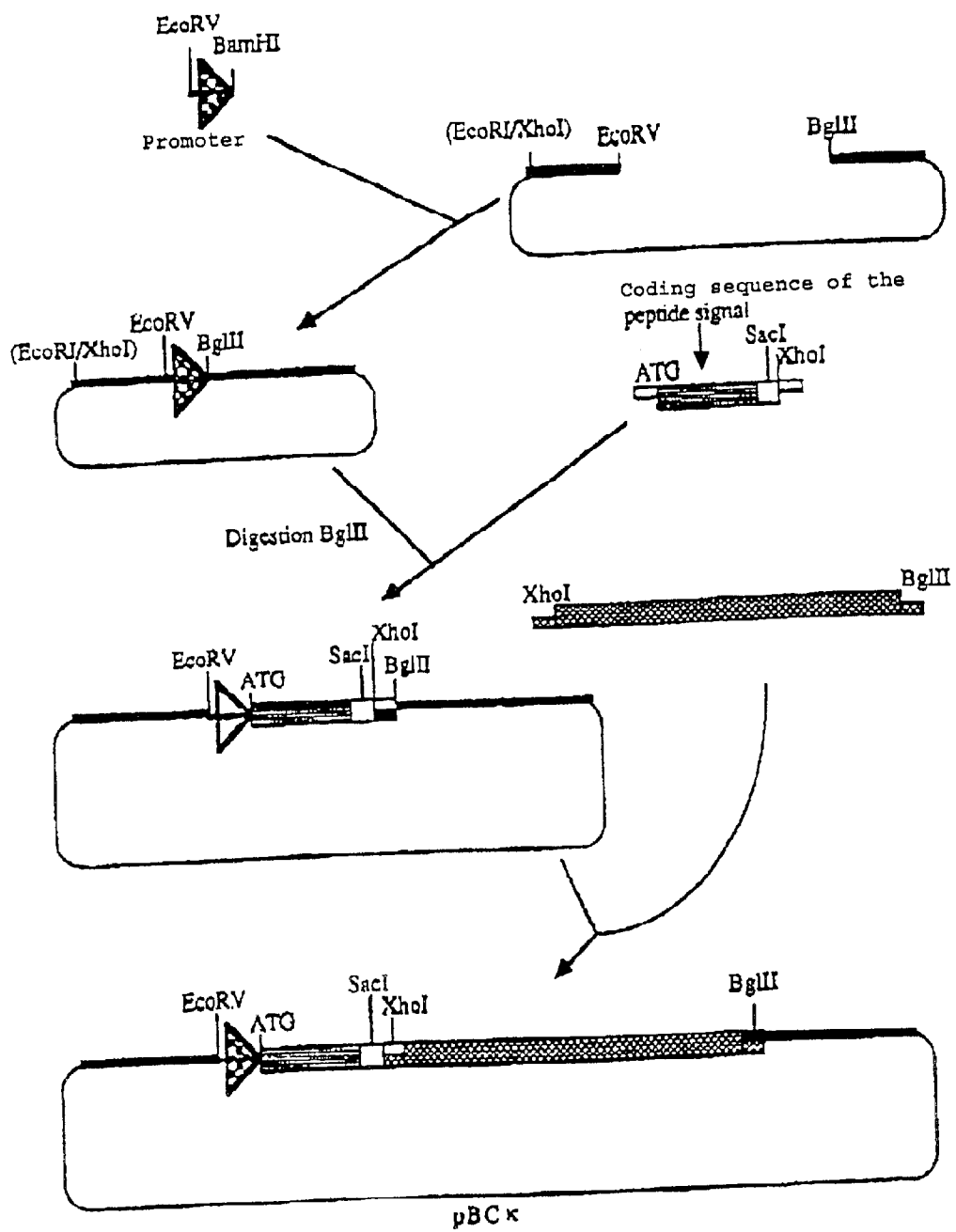
FIG. 1 illustrates the construction of a kappa light chain expression cassette, pBCK, as set forth in Example 1.

The object of the present invention is a recombinant baculovirus, characterized in that it comprises:

an expression cassette comprising a sequence coding for at least one part of an immunoglobulin H chain, which sequence is placed under transcriptional control of a first baculovirus promoter, and an expression cassette comprising a sequence coding for at least one part of an immunoglobulin L chain, which sequence is placed under transcriptional control of a second baculovirus promoter; with the first and second promoters being two different promoters which are situated at two different loci.

In accordance with one preferred mode of implementation of the present invention, the first and the second promoters are strong promoters.

In accordance with another preferred mode of implementation of the present invention, one of the promoters is situated at the site occupied in the wild baculovirus by the polyhedrin promoter and the other is situated at the site occupied in the wild baculovirus by the p10 promoter.

"Baculovirus promoter" is defined as any promoter that can be integrated into the genome of a baculovirus, and operate in insect cells; such a promoter is referred to as "strong" when it facilitates attainment of a high level of transcription (for example, on the order of that obtained with the promoters of polyhedrin or p10) from a gene placed under its control.

This definition encompasses not only the promoters of the "wild" type such as the promoters of polyhedrin and p10 of the AcMNPV or SlMNPV baculoviruses, but also the derivatives of promoters stemming from modifications of varying degrees of the sequence of a "wild" baculovirus promoter, and in particular, the synthetic or recombinant promoters, such as, for example, the synthetic promoter described by WANG et al. [Gene, 100, 131–137 (1991)].

According to one preferred embodiment of a recombinant baculovirus in accordance with the present invention, at least one of the promoters involved is selected from the group constituted by:

the promoter of polyhedrin;

the promoter of p10;

a new synthetic promoter, referred to below as the Syn promoter and constituted by a double-stranded DNA fragment with the following sequence:

coding for a signal peptide; (iii) a sequence coding for a variable domain of an H or L immunoglobulin chain; and (iv) a sequence coding for at least one part of a constant domain of an H or L immunoglobulin chain.

Such a recombinant baculovirus constitutes an expression vector that can be used directly for the production of immunoglobulins in an insect cell.

Preferably, the sequence coding for the signal peptide that is placed under the control of the first promoter and the sequence coding for the signal peptide that is placed under the control of the second promoter are two different sequences.

Sequences which are already known that code for functional signal peptides in insect cells can be used for the implementation of the present invention. As nonlimiting examples, sequences coding for function signal peptides include sequences coding for the signal peptides of Drosophila acetylcholinesterase, ovine trophoblastin, bovine lactotransferrin, the H and L chains of immunoglobulins, etc.

Nevertheless, the inventors have found that it is preferable, in order to obtain the best secretion of the immunoglobulin molecule, that the His-Val-Ser sequence be present immediately upstream of the cleavage site used by the signal peptidase, The sequences coding for the constant and variable domains can be of the same or different origins; it is also possible to use synthetic or recombinant sequences. Advantageously, the sequence coding for the constant domain is of human origin; the sequence coding for the variable domain can be of totally human origin or of at least partially nonhuman origin, for example, of murine origin, etc.

The present invention encompasses insect cells infected with a recombinant baculovirus in accordance with the invention.

The infection of cells by a double-recombinant baculovirus in accordance with the invention results in the production of H and L chains. These chains join together to reconstitute the desired monoclonal antibody which is then secreted in the culture medium.

The present invention also has as its object a procedure for the preparation of an immunoglobulin, characterized in that

```
       5-                                                               -3
ATCAAATAAATAAGTATTTTAAAGAATTCGTACGTATTTTGTATATTAATTAAAATACTATACTGTAAATAGATCG
TAGTTTATTTATTCATAAAATTTCTTAAGCATGCATAAAACATATAATTAATTTTATGATATGACATTTATCTAGCCTAG
-5
```

The sequence of the (+) strand of this fragment is identified as SEQ ID NO.: 1.

The sequence of the (−) strand of this fragment is identified as SEQ ID NO.: 2.

Use of the Syn promoter makes it possible to increase the production of recombinant antibodies in a very significant manner.

The Syn promoter as such is also part of the object of the present invention.

The p10, polyhedrin and Syn. promoters can be combined on a two plus two basis according to any combination; in particular, the Syn. promoter can be combined with the polyhedrin promoter or, advantageously, with the p10 promoter.

According to another preferred embodiment of the invention, each expression cassette comprises: (i) a strong baculovirus promoter as defined above; (ii) a sequence one cultures the insect cells infected with a recombinant baculovirus in accordance with the invention followed by extraction of the immunoglobulin from the culture medium.

The present invention also encompasses the immunoglobulins that can be produced by means of the aforementioned procedure.

The present invention also has as its object a procedure for the preparation of a recombinant baculovirus, which procedure is characterized in that:

one prepares a first transfer plasmid comprising a sequence coding for at least one part of the immunoglobulin H chain, under transcriptional control of a first strong baculovirus promoter;

one prepares a second transfer plasmid comprising a sequence coding for at least one part of the immunoglobulin L chain, under transcriptional control of a second strong baculovirus promoter; with the first and second promoters being two different promoters; and one then implements the homologous recombination of the two plasmids with the DNA of a baculovirus.

The construction of a recombinant baculovirus in accordance with the invention is implemented by using conventional heterologous genetic cloning techniques in baculoviruses.

Schematically, the construction of the transfer plasmids is implemented by insertion in a plasmid capable of replicating itself in a bacterial host (generally, E. coli) of the region of the baculovirus (for example, p10 or polyhedrin) in place of which it is desired to insert the genes coding for the immunoglobulin H or L chains. In this region, the coding sequence of the baculovirus gene (and possibly the promoter sequence of the gene) is replaced by the sequence coding for the immunoglobulin chain to be expressed (and possibly by the promoter sequence under the control of which it is desired to express this immunoglobulin chain in the case, for example, of a "derivative" promoter). The transfer plasmid obtained in this manner thus contains an insert comprising a heterologous sequence flanked by baculovirus sequences. One then co-transfects the insect cells with the DNA of the resultant transfer vector and the DNA of the baculovirus, which by homologous recombination between the viral DNA and the baculovirus sequences flanking the heterologous sequence in the plasmid enables the transfer of the foreign sequence from the plasmid into the viral genome.

According to a preferred mode of implementation of the procedure in accordance with the present invention, the transfer plasmids used carry an insert comprising an expression cassette as defined above, and on both sides of this cassette, sequences of baculoviruses which are homologous with those of the regions flanking the portion of the viral genome by replacement of which one desires to insert the said cassette.

In accordance with a preferred feature of this mode of implementation, the baculovirus sequences are homologous with those of the regions flanking the p10 gene, or homologous with those of the regions flanking the polyhedrin gene.

After replication of the viral DNA in the transfected cells, one next carries out selection of the recombinant baculoviruses that integrated the heterologous sequences.

According to an especially advantageous mode of implementation of the procedure in accordance with the invention, the baculovirus DNA with which the homologous recombination of the transfer plasmids is performed is constituted by DNA from a baculovirus that has been previously modified by insertion of two Bsu36I sites on both sides of the sequence coding for the p10 protein wherein these two Bsu36I sites are the only Bsu36I restriction sites on the genome of the modified baculovirus, and wherein the baculovirus DNA is digested by the Bsu36I enzyme.

The baculovirus in which the Bsu36I sites are inserted can be a wild baculovirus or a previously modified baculovirus, for example, the virus known as AcD3, modified by deletion of the polyhedrin gene and promoter, provided that this baculovirus preserves the regions flanking the polyhedrin and p10.

When the DNA fragments resulting from the Bsu36I digestion are brought into the presence of the two transfer vectors (by co-transfection), only those DNA fragments that recombine with the vector carrying the regions flanking the p10 reconstitute a circular viral genome and enable production of viable viruses.

Among the viruses obtained, only those that have also recombined with the vector carrying the regions flanking the polyhedrin enable the expression of the two immunoglobulin chains. The recombinants thus can be selected by detecting the immunoglobulin produced (for example, using ELISA). In addition, in the case in which the initial virus comprises the polyhedrin gene, only the viruses which recombined with the vector carrying the regions flanking the polyhedrin are lacking in this gene and can be selected on the basis of their observed phenotype (absence of polyhedrosis).

Thus, this procedure makes it possible to produce in a single step, by implementation of a triple transfection, vectors that have integrated heavy and light chains.

Increased comprehension of the present invention will be provided on the basis of the description below which refers to examples of the preparation of recombinant baculovirus in accordance with the invention and to their use for the production of immunoglobulins in insect cells.

It should be understood, however, that these examples are presented solely for the purpose of illustrating the object of the invention and do not in any manner constitute a limitation.

EXAMPLE 1

Construction of a Kappa Light Chain Cassette (pBCK) (FIG. 1)

a—Plasmid pGmAc116T:

This transfer vector is derived from the plasmid pGmAc115T [ROYER et al., J. Virol., 66, 3230–3235 (1992)], which in turn is derived from the plasmid pAc1 [CHAABIHI et al., J. Virol., 67, 2664–2671 (1993)] containing the fragment EcoRI-I from the *Autographa californica* nuclear polyhedrosis baculovirus (AcMNPV) and thus the polyhedrin gene and the sequences flanking the gene. In order to obtain pGmAc116T, the plasmid pGmAc115T was subjected to deletion of a 1900 bp fragment extending from an EcoRI site located upstream of the polyhedrin gene to a XhoI site located 1900 bp downstream of the EcoRI site. The deletion was implemented by exhaustive XhoI cleavage, followed by a partial cleavage by EcoRI. 5 µg of the plasmid pGM115T were digested for 2 hours at 37° C. by 15 units of XhoI enzyme (Boehringer) in a reaction volume of 50 µl and under the conditions specified by the supplier. The enzyme was eliminated by an extraction with phenol/chloroform and the plasmid DNA was precipitated with alcohol. This DNA was then partially cleaved by EcoRI (Boehringer) in a reaction volume of 50 µl in the presence of 0.5 unit of enzyme. Incubation was carried out at 37° C. for 20 minutes. After a new extraction with phenol/chloroform, the ends generated by the XhoI and EcoRI cleavages were made complete by Klenow's enzyme (Biolabs) in the presence of the 4 dNTPs in accordance with the protocol specified by the supplier. The plasmid DNA was then precipitated with alcohol and incubated with the ligase of the phage T4 (Boehringer) under the specified conditions. Competent E. coli bacteria were transformed by a part of the ligation mixture. Screening of the colonies from this transformation enabled selection of the plasmid pGmAc116T.

b—The Promoters:

The p10 promoter or the polyhedrin promoter from the *Spodoptera littoralis* nuclear polyhedrosis virus (SLMNPV) are amplified by PCR using primers enabling reconstitution of anEcoRV site upstream of the promoter, and a BglII site downstream. The amplification product is digested by EcoRV and BglII, and the fragments carrying the promoter sequences are inserted in pGmAc116T previously digested by the same enzymes. The digestion by EcoRV and BglII makes it possible to eliminate the AcMNPV polyhedrin promoter and to replace it with one of the two promoters cited above.

The resultant plasmids are referred to respectively as pGmAc10 (p10 promoter) and pGmAc33 (polyhedrin promoter).

The synthetic promoter was produced by chemical synthesis in the form of the two complementary oligonucleotides SEQ ID NO.: 1 and SEQ ID NO.: 2.

When they are brought together, these oligonucleotides reconstitute a double-stranded DNA that can be employed directly in a ligation reaction.

The plasmid pGmAc116T was digested by EcoRV and BglII in order to eliminate the AcMNPV polyhedrin promoter, and the sequence of the synthetic promoter was inserted as a replacement. The resultant plasmid is referred to as pGmAcSyn.

c—Signal Peptide

The coding sequence selected for the signal peptide is the following:

5'-ATG GGA TGG AGC TGT ATC ATC CTC TTC TTG GTA GCA ACA GCT ACA GGT GTC CAC TCC-3'

This sequence was selected from the sequences published by [NEUBERGER, M. S., EMBO, J., Vol. 2, p. 1373–1378 (1983)].

The sequence is identified as SEQ ID NO.: 3.

This sequence was synthesized chemically in the form of two complementary oligonucleotides with ends allowing insertion of the duplex in a BglII site. At one of the ends of the duplex, there is a sequence corresponding to that of the beginning of the framework 1 of the light chains (with the site SacI) followed by a sequence carrying a XhoI site. For the pairing, 15 µg of each of these two oligonucleotides are incubated in 50 µl of buffer (Tris 1 mM pH 7.5, EDTA 0.1 mM) for 5 minutes in a water bath at 70° C. The bath is then allowed to cool down to room temperature (22 to 25° C.). The mixture is used directly in the ligation reactions with the plasmids pGmAc10, pGmAc33 or the plasmid pGmAcSyn that have previously been cleaved by BglIII.

The ligation conditions are as follows:

1 µg of the selected plasmid pGmAc, cleaved by BglII, 1 µg of the bicatenary oligonucleotide carrying the sequence coding for the signal peptide, 2 µl of 10×ligase buffer (BOEHRINGER), distilled water q.s.p. 19 µl, 1 unit (1 µl) of ligase (BOEHRINGER); incubation is carried out at 22° C. for 2 hours; the ligation product is used for the transformation of competent E. coli bacteria.

d—Constant Region

The coding sequence of the constant region of the human κ light chain was amplified by PCR using as matrix human B lymphocyte cDNA. The human lymphocytes (approximately 5×10⁸) were prepared from 200 ml of blood using HISTOPAQUE® (SIGMA). The total RNA was extracted from these lymphocytes using a PHARMACIA kit (RNA Extraction Kit). The first cDNA strand was prepared from the total RNA using the "First-Strand cDNA Synthesis Kit" from PHARMACIA.

The primers used for amplification of the Cκ cDNA are as follows:

HuCκBAC:

5'-AG CTC GAG ATC AAA CGG-3'

(the XhoI site is underlined).

This primer corresponds to a consensus sequence on the 3' end of the sequences coding for the variable domains of the light chains of human immunoglobulins (Jκ) and contain an XhoI cleavage site.

It is identified as SEQ ID NO.: 4.

HuCκFOR:

5'-GAA GAT CT A ACA CTC TCC GCG GTT GAA G-3'

(the BglII site is underlined).

This primer is complementary with the 3' end of the human CK genes and carries a BglII site downstream of the stop codon TAG.

It is identified as SEQ ID NO.: 5.

Amplification with the primers HuCκBAC and HUCκFOR produced an approximately 340 bp fragment containing the totality of the CK region flanked by the XhoI and BglII sites.

The amplification product was digested by BglII and XhoI before being cloned in the XhoI-BglII sites of the pGmAc plasmids carrying the sequence coding for the signal peptide, yielding the plasmid pBCK.

The composition of the ligation mixture is the following: 1 µg of the plasmid pCmAc cleaved by XhoI and BglII; 200 ng of the Ck fragment that had been amplified and digested by BglII and XhoI; 2 µl of 10×ligase buffer (BOEHRINGER), distilled water q.s.p. 19 µl, 1 unit (1 µl) of ligase (BOEHRINGER).

Incubation is carried out at 22° C. for 2 hours; the ligation product is used for the transformation of competent E. coli bacteria.

EXAMPLE 2

Figure 2:
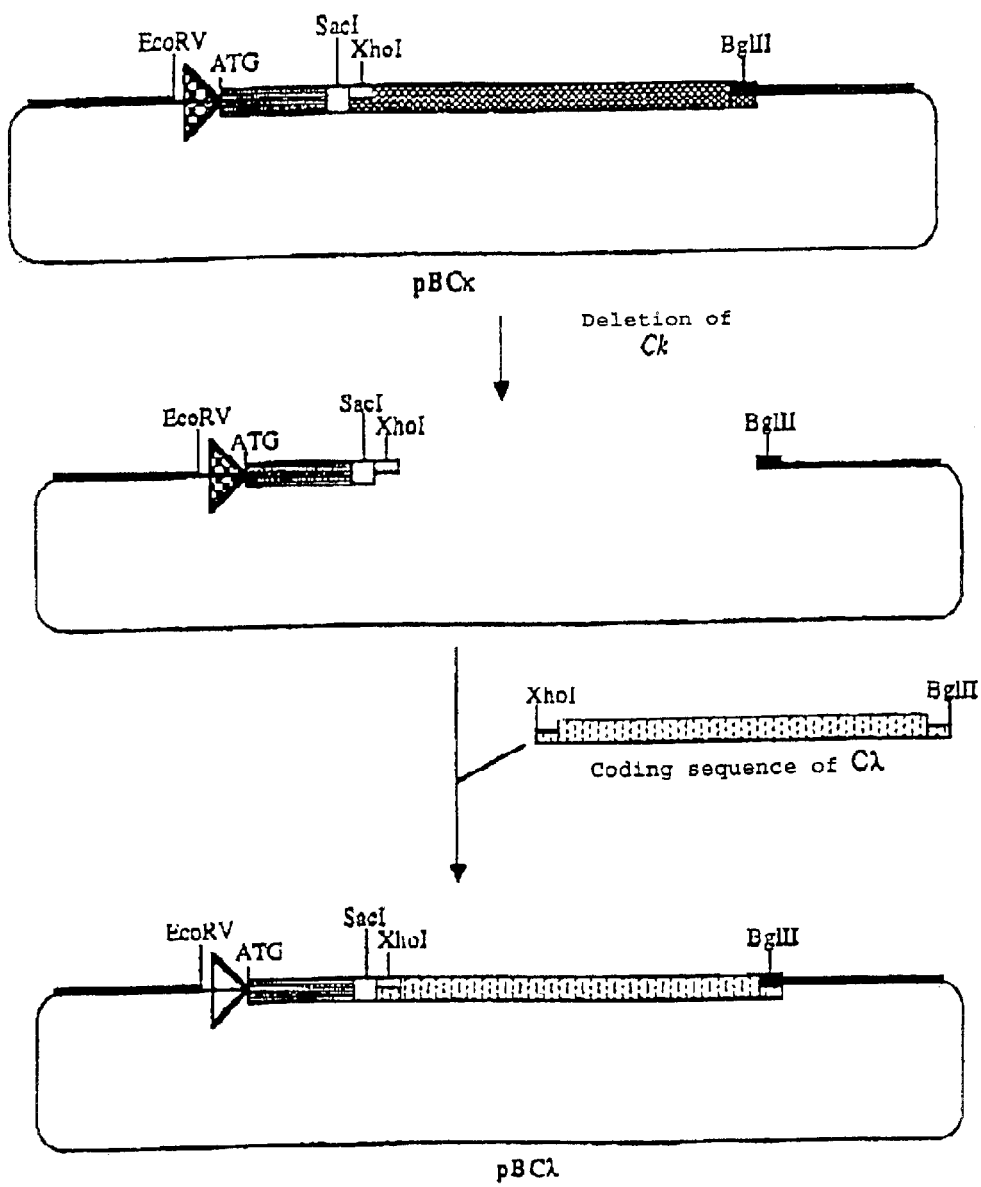
FIG. 2 illustrates the construction of the lambda light chain expression cassette, pBCλ, as set forth in Example 2.

Lambda Light Chain Cassette (pBCλ) (FIG. 2)

a. Constant Region Cλ:

As for the coding sequence of the constant region Cκ the coding sequence Cκ was obtained by PCR amplification of the complementary DNA of the messenger RNA from human B lymphocytes.

PCR amplification of the region Cλ was performed in the presence of the primer OPP-HuCλ3', which is complementary to the 3' end of the Cλ region and has the BglII restriction site, and the primer OPP-HuCλ5', which is complementary to the 5' end of the Cλ regions and has the XhoI restriction site.

The sequences of the two primers are as follows:

OPP-HuCλ3':

5'-CCT GTC AGA TCT ATG AAC ATT CTG TAG GGG-3'

(BglII site underlined).

This primer is identified as SEQ ID NO.: 6.

OPP-HuCλ5':

5'-CCG CCC TCC CTC GAG CTT CAA-3'

(XhoI site underlined).

This primer is identified as SEQ ID NO.: 7.

After cleavage by the enzymes BglII and XhoI, the amplified sequence Cλ is inserted between the XhoI and BglII sites of the plasmid PBCK, which has previously been subjected to deletion of the Cκ gene by treatment with the enzymes BglII and XhoI and purification of the 7.8 kb plasmid fragment.

The resultant plasmid is referred to as pBCλ.

The insertion of the constant lambda region was verified by sequencing of the plasmid pBCλ in the presence of the two primers OPP-HuCλ3' and OPP-HuCλ5'.

The lambda chain (Cλ) cassette is intended for the cloning of the variable parts of lambda type light chains.

These variable regions are amplified by PCR using, on the one hand, a primer (OPP-HuVλ5') that hybridizes at the level of the framework 1 of the light chains and enables reconstitution of a SacI site and, on the other hand, a primer (OPP-HuVλ3') which is almost complementary to the primer OPP-HuCλ5' and which enables reconstitution of a XhoI site.

The sequences of these primers are as follows:

OPP-HuVλ5':

5'-CA (GC) TCTGAGCTCAC (GT) CAG-3'

(SacI site underlined).
This primer is identified as SEQ ID NO.: 8.
OPP-HuVλ3':

5'-TTG AAG CTC CTC GAG GGA GGG CGG GAA-3'

(XhoI site underlined).
This primer is identified as SEQ ID NO.: 9.

EXAMPLE 3

Heavy Chain γ1 Cassette (pBCγ1) (FIG. 3)
a—Transfer Plasmid

The plasmid pGm16 [BLANC et al., Virology, 192, 651–654 (1993)] is derived from a plasmid in which had been cloned the fragment EcoRI-P of the baculovirus AcMNPV containing the gene p10. Almost the entire coding sequence was deleted and replaced by a BglII site enabling insertion of expression sequences under the control of the p10 promoter.

b—The Signal Peptide

The coding sequence of the signal peptide for the secretion of the heavy chain is an artificial sequence that codes for a peptide having two characteristics that promote secretion: overall hydrophobicity (this characteristic is common to all of the signal peptides) and the presence of the Val-His-Ser upstream of the site of the cleavage by the "Signal Peptidase".

The coding sequence of this signal peptide is the following:

5'-ATG GCT GTC CTG GTG CTG TTC CTC TGC CTG GTT GCA TTT CCC AGC TGT GTC CAC TCC-3'

It is identified as SEQ ID NO.: 10.

Figure 3:
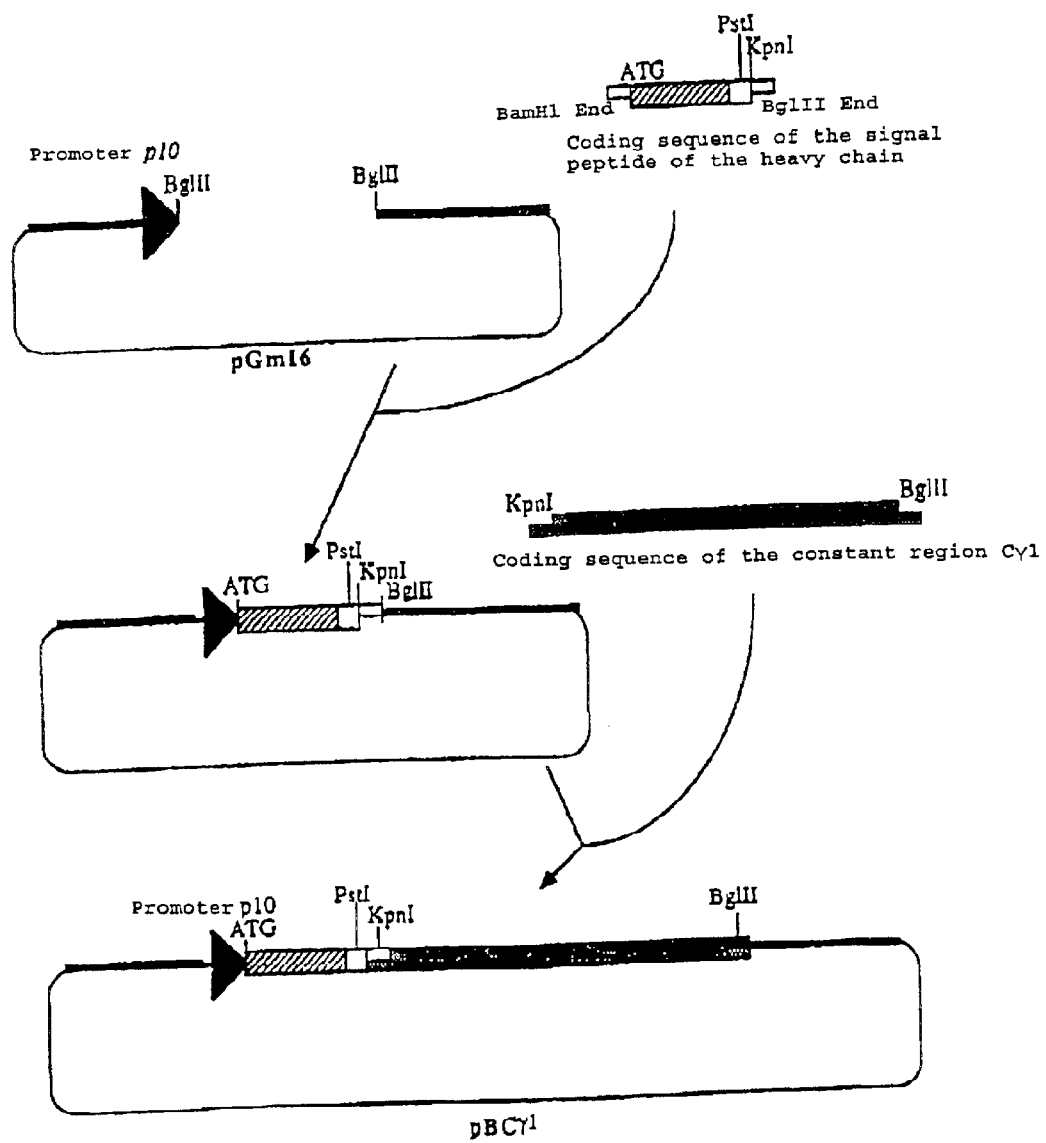
FIG. 3. illustrates the construction of the heavy chain □1 expression cassette, pBCα1, as set forth in Example 3.

It was synthesized chemically in the form of complementary strands such that it can be inserted in a BglII site (FIG. 3). The pairing and ligation conditions are identical to those employed for the cloning of the coding sequence of the signal peptide used for the light chain.

c—Human Constant Regions:

IgG1 (Cγ1)

The cDNA of the coding sequence of the human Cγ1 was amplified by PCR using the following primers:

HuCγ1BAC:

5'CAA GGT ACC ACG GTC ACC GTC TCC-3'

(KpnI site underlined).

This primer corresponds to a consensus sequence of the human JH regions (3' ends of the variable regions of human heavy chains) and comprises a KpnI site.
This primer is identified as SEQ ID NO.: 11.

HuCγ1FOR:

5'-GAAGATC TCA TTT ACC CGG AGA CAG GGA G-3'

(BglII site underlined).
This primer is identified as SEQ ID NO.: 12.

The sequence was determined from human Cγ1 sequences. The primer is complementary to the 3'end of human Cγ1 and enables reconstitution after amplification of a BglII site downstream of the stop codon.

The matrix employed for amplifying the human Cγ1 region is the same mixture of cDNA that was used for amplification of the coding sequences Cκ and Cλ.

The amplification product was sequenced and cloned in the transfer vector pCm16 carrying the sequence coding for the signal peptide. The resultant construction was referred to as pBCγ1 (FIG. 3).

For amplification of the constant regions of the immunoglobulins IgG2, IgG3, IgG4, IgE, IgM and IgA, one uses as the 5' primer the primer HuCγ1BAC above combined respectively with the following 3' primers:

IgG2:

HuCγ1FOR,

IgG3:

HuCγ1FOR,

IgG4:

HuCγ1FOR,

IgE:

5'-GAAGATCTCATTT ACC GGG ATT TAC AGA-3', identified as SEQ ID NO.: 13,

IgM:

5'-GAAGATC TCA TTT ACC GGT GGA CTT GTC GTC-3', identified as SEQ ID NO.: 14;

IgA:

5'-GAAGATCTCA GTA GCA GGT GCC GTC CAC CTC-3' identified as SEQ ID NO.: 15.

For the constant regions of IgG1, 2, 3 and 4, the same primer is used as the 3' primer because of the high conservation of sequences among the different subclasses in this region. For the primers employed for IgE, IgM and IgA, the BglII cleavage sites introduced are underlined.

EXAMPLE 4

Expression of a Chimeric Antibody (Mouse-human) in the Insect Cells Infected by a Vector in Accordance with the Invention K20 mAB is a murine antibody produced by a hybridoma. It is directed again the β subunit of the CD29 receptors of the lymphocytes [BOUMSELL et al., J. Exp. Med. 152, p. 229 (1980)]. A recombinant baculovirus in accordance with the invention was used to express a K20 chimeric antibody having the variable regions of the original K20 and the human constant regions stemming from the cassettes pBCκ and pBCγ1.

a—Cloning of the variable region of the light κ chain of K20:

The total RNA of the hybridoma was extracted using the "RNA Extraction Kit" of PHARMACIA, and an inverse transcription was performed using the primer VKFOR (First-Strand cDNA Synthesis Kit: PHARMACIA):

VKFOR

5'-CCG TTT GAT CTC GAG CTT GGT CCC 3'

(XhoI site underlined)
identified as SEQ ID NO.: 16.

This primer is complementary to the consensus sequence at the end 3' of the variable region Vκ of the murine genes. It is intended to amplify the Vκ rearranged with the Jκ1 or Jκ2 junctions (which are the most plentiful) but also with those rearranged with the Jκ4 or Jκ5 junctions.

The cDNA was amplified by PCR using, on the one hand, the primer VκFOR and, on the other hand, the primer Vκ2BAC:

Vκ2BAC:

5'GAC ATT CAG CTC ACC CAG TCT CCA-3'

(SacI site underlined)
identified as SEQ ID NO.: 17.

The sequence of this primer is identical to a previously published sequence [WINTER and CLACKSON, Nature, 352, p. 624 (1991)]. V□2BAC has the capability of amplifying the murine variable regions Vκ3, Vκ4 and Vκ6.

Figure 4:
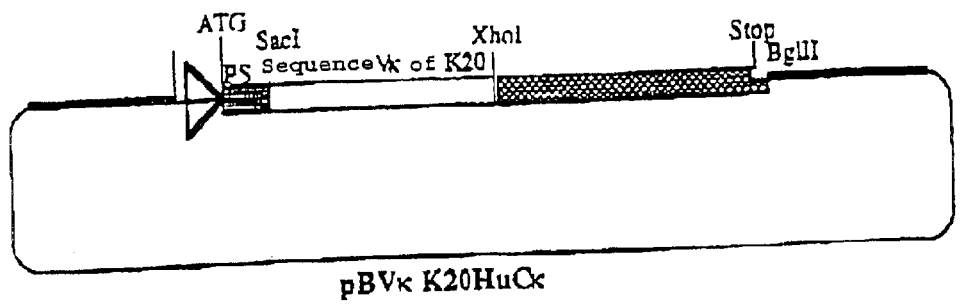
FIG. 4 (Parts a and b) illustrates vectors encoding (a) the variable region of the light kappa chain of K20 mAb and (b) the variable region of the light chain γ1 of K20 mAb.
Figure 4:
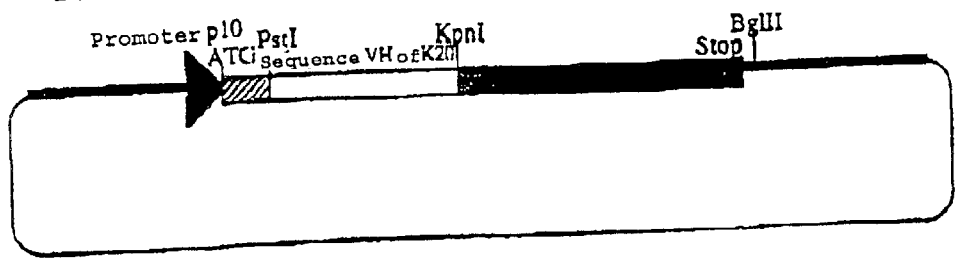

After amplification of the region VκK20, a SacI-Xho1 digestion of the amplification product was performed and the resultant fragment was cloned between the SacI and Xho1 sites of the light chain plasmid pBCκ, yielding the plasmid pBVκK20HuCκ (FIG. 4a).

b—Cloning of the variable region of the light chain γ1 of K20:

Inverse transcription on the total RNA extracted from the hybridoma producer of K20 was performed using the primer VHFOR. This primer as well as the primer VH1BAC were then used to amplify the VH from the cDNA:

VHFOR:

5'-TGA GGA GAC GGT GAC CGT GGT aCC TTG GC-3'

(KpnI site underlined)
identified as SEQ ID No. 18.

VH1BAC:

5'-AG GT(C/G) (A/C)A(A/G) CTG CAG (C/G) AG TC(A/T) GG-3'

(PstI site underlined)
identified as SEQ ID NO.: 19.

VHFOR is identical to a primer described by ORLANDI et al. (1989. Proc. Natl. Acad. Sci. USA 86, 3833–3837), with the sole difference being the substitution of the "a" which replaces a "C" (cf. KpnI site underlined above).

Figure 5:
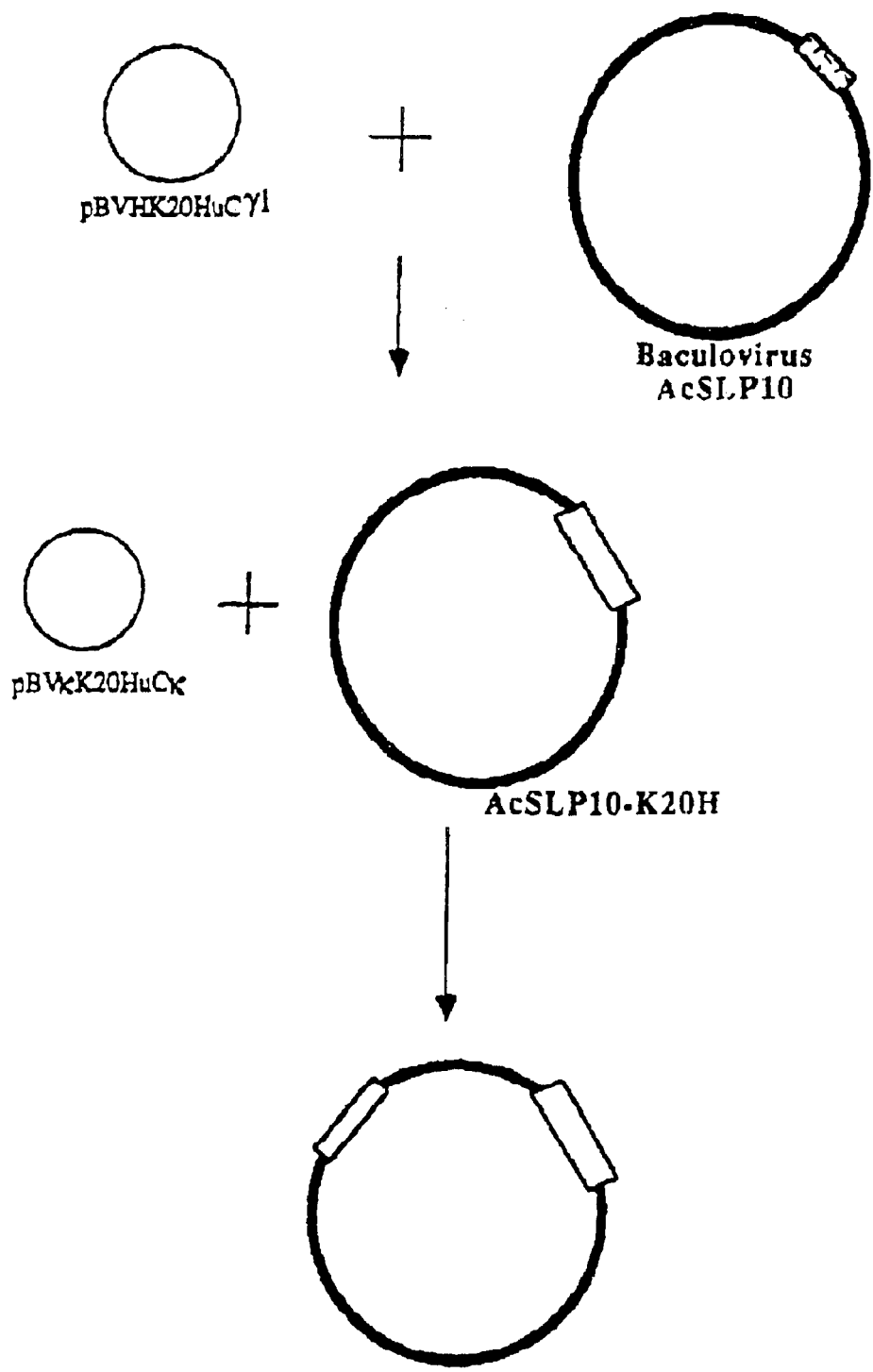
FIG. 5 illustrates the construction of a recombinant virus producing chimeric K20.

After amplification and digestion by PstI and KpnI, the VH region of K20 was inserted in the heavy chain plasmid at the PstI-KpnI sites. The charged plasmid was named pBVHK20HUCγ1 (FIG. 4B).

c—Construction of a Recombinant Virus Producing Chimeric K20 (FIG. 5)

1—Insertion of the Heavy Chain:

The charged plasmid pBVHK20HUCγ1 was used in co-transfection with the DNA from a modified baculovirus called AcSLp10 [CHAABIH] et al., J. Virol., 67, 2664–2671 (1993)], which is lacking in the polyhedrin gene (promoter+coding sequence) but carries the coding sequence of polyhedrin under control of the p10 promoter in the natural p10 locus. Since this virus produces polyhedrosis in infected cells, the recombination at the level of the p10 locus can thus be easily detected. The co-transfection conditions are the following: 500 ng of viral DNA are mixed with 5 μg of plasmid DNA and 40 μl of DOTAP solution (BOEHRINGER) in 3 ml of serum-free culture medium for insect cells. This mixture is used to cover $4 \times 10^6$ Sf9 cells (ATCC35CRL 1711); after 4 hours of contact, the co-transfection mixture is replaced by 4 ml of complete medium and incubation is carried out at 27° C. for 5 days.

After the co-transfection, the virus producing the heavy chain of the chimeric antibody K20 under the control of the p10 promoter was purified using the lysis plate technique. This virus was named AcSLp10-K20H.

2—Insertion of the Light Chain

The charged plasmid pBVκK20HUCK was used in co-transfection with the DNA from the modified baculovirus AcSLp10-K20H.

The recombinant doubles were selected by the limit dilution technique combined with ELISA and/or molecular hybridization.

After the co-transfection, a range of dilutions is made from the infectious supernatant, and each dilution is used for the infection of insect cells. Three days after the infection, the supernatants are tested on ELISA to determine the presence of correctly assembled human-type antibodies. The supernatants from the wells that are the most positive for the highest dilutions are in turn diluted and used to infect other cultures; after several dilution/infection cycles, the supernatants enriched in baculovirus producing the entire antibody are spread on a cell sheet and cloned by the lysis plate method.

EXAMPLE 5

Production and Purification of the K20 Antibody

The double-recombinant virus was amplified by a series of passages over insect cells in culture. The viral stock was then used to infect a culture agitated in a spinner (500 ml of culture at $10^6$ cells per ml).

After 72 hours of infection, the culture was collected and centrifuged at 1000 g in order to clarify the supernatant. The supernatant was concentrated to ⅓ of its initial volume by centrifugation through a membrane having a single 30-kDa slit (CENTRIPEP 30, Amicon) (first centrifugation: 1000 g, 20° C., 30 minutes: elimination of the filtrate; second centrifugation: 1000 g, 20° C., 20 minutes).

The solution was equilibrated in a fixation buffer on protein A, by dilution in this buffer followed by an additional concentration by centrifugation (dilution buffer: glycerol 1.5 M, NaCl 3M; pH 8.9). The equilibrated solution is then passed into a column of protein A, itself equilibrated in the same buffer as the K20 solution. After rinsing of the column, the antibody is eluted by an elution buffer (acetate 0.1 M, NaCl 0.5 M; pH 3). The elution is followed by measuring the OD at 280 nm. The fractions containing the antibodies were mixed and concentrated by centrifugation through a membrane with a single 10-kDa slit (CENTRIPEP 10, AMICON). The concentrated solution is diluted with PBS and then reconcentrated in the same manner. The resultant antibody solution is stored at +4° C. in PBS (137 mM NaCl; 2.7 mM KCl; 4.3 mM $Na_2HPO_4\text{-}7H_2O$; 1.4 mM $KH_2PO_4$)

The amount of antibodies was determined by electrophoresis on polyacrylamide-SDS gel, using as control a commercial human IgG1 (SIGMA). This investigation showed that the unreduced chimeric antibody (disulfide bridges intact) migrates to the same level as the control human antibodies.

After treatment with dithiothreitol (DTT), two bands appeared that corresponded to the heavy and light chains, and migrating to the same level as the chains from the control human antibody that had also been reduced in DTT.

In order to confirm the preceding results, the proteins from the fractions comprising the antibodies were transferred to a nitrocellulose membrane, and the H and L chains were detected by specific antibodies for the human Cγ1 and Cκ regions.

This test demonstrated that the antibodies produced by the insect cells are definitely constituted of H and L chains and that the constant regions of these chains are recognized by the specific antibodies.

EXAMPLE 6

Test of the Activity and Specificity of the K10 Produced by the Insect Cells

The monoclonal antibody K20 is directed against the β1 subunit of the human integrins (CD29 receptor) located at the surface of the lymphocytes. The fixation of K20 on the CD29 molecule inhibits the proliferation of activated human T4 lymphocytes [GROUX et al., Nature, 339, 152–154 (1989)]. The suppressive effect of K20 on T cell proliferation provides a basis for envisaging the use of this antibody in the prevention of graft rejection. In order to test the activity of chimeric K20 antibody produced in accordance with the invention, two types of experiments were carried out: immunofluorescence and inhibition of T lymphocyte proliferation. The experimental protocols employed have essentially been previously described [GROUX et al., Nature 339, 152–154 (1989); TICCHIONI et al., Journal of Immunology 151, 119–127 (1993)].

a—Immunofluorescence Experiments

Human lymphocytes carrying the CD29 receptor were fixed on glass slides then incubated in the presence of the chimeric K20 produced in accordance with the invention, in the presence of K20 of murine origin, or in the presence of buffer only.

After a series of rinsings, either a fluorescent specific secondary antibody of the chimeric K20 produced in accordance with the invention or a fluorescent specific secondary antibody of the K20 of murine origin was added.

After an additional rinsing, the preparations were examined under the microscope to visualize the fluorescence which showed that the chimeric K20 produced in accordance with the invention becomes attached in a specific manner to the lymphocytes carrying CD29, like the positive control K20 of murine origin; no fluorescence was detected in the absence of the K20 antibodies.

b—Inhibition of the Proliferation of CD4$^+$ Lymphocytes by K20

Human CD4$^+$ lymphocytes were activated by an anti-CD3 antibody in the presence of interleukin-2. Chimeric K20 antibodies in accordance with the invention or K20 of murine origin were added (20 µg/ml) to examine their effect on lymphocyte proliferation. A test with a non-inhibitory antibody [GROUX et al., Nature, 339, p. 152 (1989)] was carried out as a negative control.

Proliferation is measured by counting the amount of $^3$H thymidine incorporated after 4 days of culture following the treatments with the antibodies. A level of inhibition of proliferation of 50 to 70% was found when the cells were incubated with the K20 antibody produced in accordance with the invention.

The K20 antibody of murine origin (positive control) also inhibits proliferation of the activated lymphocytes at the same levels: 50 to 70%.

EXAMPLE 7

Comparison of the Efficacy of the Syn Promoter and the Polyhedrin Promoter

Two double-recombinant viruses were constructed in accordance with the protocol described in Examples 1 to 4 above.

in one of the viruses (virus 1), the heavy chain is under control of the p10 promoter and the light chain is under control of the polyhedrin promoter;

in the other virus (virus 2), the heavy chain is under control of the p10 promoter and the light chain is under control of the Syn promoter.

The amounts of antibodies secreted by the infected cells by these two viruses were determined as described in Example 5.

The results are shown in Table I below, which displays the amount of antibodies secreted (in µg/ml) at different post-infection time periods:

TABLE I

| Virus | 12 hours post-infection | 24 hours post-infection | 48 hours post-infection |
|---|---|---|---|
| 1 | 0.31 | 0.96 | 8.9 |
| 2 | 1.24 | 2.72 | 9.9 |

These results demonstrate that the secretion of antibodies takes place earlier and in larger quantities when the Syn promoter is employed.

What is claimed is:

1. A recombinant baculovirus comprising an expression vector for use in the production of immunoglobulins in an insect cell, said expression vector comprising:
   a first expression cassette comprising a first sequence coding for at least one part of an immunoglobulin H chain, wherein said first sequence is under transcriptional control of a first baculovirus promoter,
   a second expression cassette comprising a second sequence coding for at least one part of an immunoglobulin L chain, wherein said second sequence is under transcriptional control of a second baculovirus promoter; wherein
   said first baculovirus promoter and said second baculovirus promoter are two different promoters and are located at two different loci.

2. The recombinant baculovirus in accordance with claim 1, wherein one of said first and second baculovirus promoters is located at a site occupied in wild baculovirus by a polyhedrin promoter and said other baculovirus promoter of said first and second baculovirus promoters is located at a site occupied in the baculovirus by a p10 promoter.

3. The recombinant baculovirus in accordance with claim 1 or 2, wherein said first and second baculovirus promoters are strong promoters, wherein said strong promoters are at least as strong as a polyhedrin promoter or a p10 promoter.

4. The recombinant baculovirus in accordance with claim 1 wherein each of said first and second expression cassettes comprises: (i) a strong baculovirus promoter at least as strong as a polyhedrin promoter or a p10 promoter and, under the control of said baculovirus promoter: (ii) a sequence coding for a signal peptide; (iii) a sequence coding for a variable immunoglobulin domain; and (iv) a sequence coding for a constant domain of an immunoglobulin H or L chain.

5. An insect cell infected by a recombinant baculovirus in accordance with claim 1.

6. A process for preparing a recombinant baculovirus in accordance with claim 1 comprising the steps of:
   preparing a first transfer plasmid comprising a sequence coding for at least one part of an immunoglobulin H chain, under transcriptional control of a first strong baculovirus promoter at least as strong as a polyhedrin promoter or p10 promoter;
   preparing a second transfer plasmid comprising a sequence coding for at least one part of an immunoglobulin L chain, under transcriptional control of a second strong baculovirus promoter, at least as strong as a polyhedrin promoter or p10 promoter wherein said first and second promoters are two different promoters;
   performing homologous recombination of the two plasmids with baculovirus DNA;
   allowing replication of viral DNA in transfected cells;
   selecting recombinant baculoviruses that have integrated the sequence coding for at least one part of the immunoglobulin H chain and the sequence coding for at least one part of the immunoglobulin L chain.

7. The recombinant baculovirus in accordance with claim 3, wherein at least one of the first and second baculovirus promoters is selected from the group consisting of:
   a p10 promoter;
   a polyhedrin promoter; and
   a synthetic promoter, defined as Syn promoter and comprising a double-stranded DNA fragment having one of the following sequences:

5-ATCAAATAAATAAGTATTTTAAAGAATTCGTACGTATTTTGTATATTAATTAAAATACTATACTGTAAATAGATCG-3 (SEQ ID NO:1)

3-TAGTTTATTTATTCATAAAATTTCTTAAGATGCATAAAACATATAATTAATTTTATGATATGACATTTATCTAGCCTAG-5 (SEQ ID NO:2).

8. The recombinant baculovirus in accordance with claim 4, wherein said sequence coding for a signal peptide of said first expression cassette is different from said sequence coding for a signal peptide of said second expression cassette.

9. The recombinant baculovirus in accordance with claim 4, wherein at least one of the sequences coding for a signal peptide codes for a peptide that has an His-Val-Ser signal immediately upstream of a cleavage site used by a signal peptidase.

10. The recombinant baculovirus in accordance with claim 4, wherein at least one of said sequences coding for a constant immunoglobulin domain is a sequence of human origin.

11. A method for preparing immunoglobulin comprising the steps of:

infecting at least one insect cell with a recombinant baculovirus, said recombinant baculovirus comprising an expression vector comprising 1) a first expression cassette comprising a first sequence coding for at least one part of an immunoglobulin H chain, wherein said first sequence is under transcriptional control of a first baculovirus promoter and 2) a second expression cassette comprising a second sequence coding for at least part of an immunoglobulin L chain, wherein said second sequence is under transcriptional control of a second baculovirus promoter, wherein said first baculovirus promoter and said second baculovirus promoter are two different promoters and are located at two different loci;

culturing at least one insect cell in a culture medium and extracting said immunoglobulin from the culture medium.

12. The process according to claim 6, wherein each of said first and second transfer plasmids carries an insert comprising:

an expression cassette comprising a strong baculovirus promoter at least as strong as a polyhedrin promoter or a p10 promoter and, under the control of said promoter, a sequence coding for a signal peptide, a sequence coding for a variable immunoglobulin domain, and a sequence coding for a constant domain of an immunoglobulin H or L chain, said expression cassette flanked on each side by baculovirus sequences homologous with those of the regions flanking the portion of the viral genome being replaced by said expression cassette.

13. The process according to claim 12, wherein said baculovirus sequences are homologous with sequences of the regions flanking the p10 gene or with sequences of the regions flanking the polyhedrin gene.

14. The process according to claim 13, wherein said baculovirus DNA comprises DNA from a baculovirus having a Bsu36I site on each side of the sequence coding for the p10 protein, wherein said two Bsu36I sites are the only Bsu36I sites of said baculovirus DNA and wherein said baculovirus DNA is digested by the enzyme Bsu36I.

* * * * *